(12) United States Patent
Hakala et al.

(10) Patent No.: US 11,710,558 B2
(45) Date of Patent: Jul. 25, 2023

(54) COMPUTER MODELING FOR FIELD GEOMETRY SELECTION

(71) Applicant: SIEMENS HEALTHINEERS INTERNATIONAL AG, Steinhausen (CH)

(72) Inventors: Mikko Hakala, Rajamaki (FI); Esa Kuusela, Espoo (FI); Elena Czeizler, Helsinki (FI); Shahab Basiri, Siuntio (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 204 days.

(21) Appl. No.: 17/029,799

(22) Filed: Sep. 23, 2020

(65) Prior Publication Data

US 2022/0093242 A1    Mar. 24, 2022

(51) Int. Cl.
*G16H 40/40* (2018.01)
*G16H 20/40* (2018.01)
*G16H 40/67* (2018.01)
*G16H 40/20* (2018.01)
*G16H 10/60* (2018.01)
*G16H 15/00* (2018.01)
*G16H 50/70* (2018.01)
(Continued)

(52) U.S. Cl.
CPC ............ *G16H 40/40* (2018.01); *A61N 5/1031* (2013.01); *A61N 5/1038* (2013.01); *A61N 5/1081* (2013.01); *G16H 10/60* (2018.01); *G16H 15/00* (2018.01); *G16H 20/40* (2018.01); *G16H 40/20* (2018.01); *G16H 40/67* (2018.01); *G16H 50/20* (2018.01); *G16H 50/70* (2018.01); *G16H 70/20* (2018.01); *A61N 2005/1074* (2013.01)

(58) Field of Classification Search
CPC .. A61N 5/1031; A61N 5/1038; A61N 5/1081; A61N 2005/1074; G16H 10/60; G16H 15/00; G16H 20/40; G16H 40/20; G16H 40/67; G16H 50/20; G16H 50/70; G16H 70/20; G16H 40/63; G16H 40/40
See application file for complete search history.

(56) References Cited

U.S. PATENT DOCUMENTS

2005/0043965 A1*  2/2005  Heller .................... G16H 20/10
                                                                                  705/2
2012/0136194 A1*  5/2012  Zhang .................... A61N 5/103
                                                                                  600/1

(Continued)

*Primary Examiner* — Jason S Tiedeman
*Assistant Examiner* — Liza Tony Kanaan
(74) *Attorney, Agent, or Firm* — Foley & Lardner LLP (57) ABSTRACT

Disclosed herein are systems and methods for identifying radiation therapy treatment data for different patients, such as field geometry. A central server collects patient data, radiation therapy treatment planning data, clinic-specific rules, and other pertinent treatment/medical data associated with a patient. The server then executes one or more machine-learning computer models to predict field geometry variables and weights associated with the patient's treatments. Using the predicted variables and weights, the server execute a clinic-specific set of logic to identify suggested field geometry, such as couch/gantry angles and/or arc attributes. The server then monitors whether end users (e.g., medical professionals) revise the suggested field geometry and trains the model accordingly.

20 Claims, 6 Drawing Sheets

(51) Int. Cl.
  *G16H 50/20* (2018.01)
  *G16H 70/20* (2018.01)
  *A61N 5/10* (2006.01)

(56) References Cited

U.S. PATENT DOCUMENTS

2019/0030370 A1* 1/2019 Hibbard ............... A61N 5/1067
2020/0289847 A1* 9/2020 Sjölund ............... A61N 5/1039

* cited by examiner

```
{
  "Type": "FieldGeometry",
  "fields": [
    {                                          {
      "CollimatorAngle": 15.0,                   "CollimatorAngle": 15.0,
      "CouchAngle": 0.0,                         "CouchAngle": 90.0,
      "GantryEnd": 225.3,                        "GantryEnd": 270.0,
      "GantryStart": 129.0,                      "GantryStart": 30.0,
      "IsocenterX": 127.46,                      "IsocenterX": 127.46,
      "IsocenterY": 101.21,                      "IsocenterY": 101.21,
      "IsocenterZ": 75.0,                        "IsocenterZ": 75.0,
      "Type": "typeVMAT1",                       "Type": "typeVMATrot1",
      "X1jaw": -42.793,                          "X1jaw": -43.793,
510   "X2jaw": 46.508                      530   "X2jaw": 47.508
    },                                         },
    {                                          {
      "CollimatorAngle": 345.0,                  "CollimatorAngle": 345.0,
      "CouchAngle": 0.0,                         "CouchAngle": 90.0,
      "GantryEnd": 225.3,                        "GantryEnd": 270.0,
      "GantryStart": 129.0,                      "GantryStart": 30.0,
      "IsocenterX": 127.46,                      "IsocenterX": 127.46,
      "IsocenterY": 101.21,                      "IsocenterY": 101.21,
      "IsocenterZ": 75.0,                        "IsocenterZ": 75.0,
      "Type": "typeVMAT2",                       "Type": "typeVMATrot2",
      "X1jaw": -45.042,                          "X1jaw": -43.042,
520   "X2jaw": 50.306                      540   "X2jaw": 49.306
    },                                         }
  ],
  "patId": "P_098"
}
```

COMPUTER MODELING FOR FIELD GEOMETRY SELECTION

TECHNICAL FIELD

This application relates generally to generating, training, and operating computer models to identify and optimize radiation therapy treatment procedures.

BACKGROUND

Radiation therapy treatment planning (RTTP) is a complex process that contains specific guidelines, protocols and instructions adopted by different medical professionals, such as the clinicians, the manufacturers of the medical device, the treating physicians, and the like. Due to the extreme nature of radiation emitted from the radiotherapy machine, it is imperative that all the instructions are precisely followed. Field Geometry, as used in the context of RTTP, refers to various attributes of a radiotherapy machine while the patient is receiving the prescribed radiotherapy dose. For instance, the prescribing physician may identify a source location (e.g., patient's organ to be treated or tumor to be eradicated) and a corresponding dosage. Moreover, other parties (e.g., clinicians or machine manufacturer) may determine positioning attributes (e.g., angles) of the gantry and the patient on the couch to receive optimum treatment.

Conventionally, identifying and applying guidelines to implement radiation therapy treatment are performed by the clinician/technician. For instance, selecting the most suitable field geometry for a patient is one aspect of RTTP that has been delegated to clinicians who use their subjective understanding and skill in conjunctions with various external and internal guidelines to identify optimum field geometry for each patient. However, this conventional method is inefficient.

For instance, as the first step of the field geometry selection, treating physicians may identify the treatment modality (e.g., choose between the volumetric modulated arc therapy (VMAT) or Intensity-modulated radiation therapy (IMRT)). Treating physicians may then decide whether a coplanar or non-coplanar treatment is preferred. Treating physicians may then determine beam limiting device angles for the treatment. In the case of IMRT, the beam delivery directions and number of beams are the specifically relevant variables that must be decided, whereas for VMAT, the technician may need to choose the number of arcs and their corresponding start and stop angles. For these decisions, each provider clinic and technician may have his or her own preferences and practices. For instance, a technician may place the radiation isocenter directly onto the subject area (e.g., tumor) and may decide to have a full arc of gantry motion around the subject area. Another technician may approach the same RTTP by having a few fixed field directions and attempt to avoid other organs. Therefore, the same RTTP may be interpreted in different ways, which has produced undesirable results.

SUMMARY

For the aforementioned reasons, there is a desire for unified computer modeling methods and systems to generate RTTP based on physician instructions that can be implemented by different clinics and technicians. There is a desire for a computer model to generate RTTP, such that calculating field geometry (or other attributes of the radiation therapy treatment) is no longer dependent on the technician's subjective interpretation. The methods and systems described herein provide a formalized approach to selecting/identifying the field geometry in a single automated framework, which can involve both guidelines and automated models.

In an embodiment, a method comprises receiving, by a server, radiation therapy treatment planning data associated with treatment of a patient, the radiation therapy treatment planning data further comprising at least a patient identifier; retrieving, by the server using the patient identifier, anatomy data associated with the patient; retrieving, by the server using a clinic identifier, a file comprising clinic-specific logic indicating treatment attributes of a radiotherapy machine in accordance with at least one of radiation therapy treatment planning data or patient anatomy; executing, by the server, one or more machine-learning model using the radiation therapy treatment planning data, anatomy data, and clinic-specific logic to identify one or more variables, wherein the one or more machine-learning models is trained based on previously performed radiation therapy treatments and corresponding patient data and clinic-specific logic; executing, by the server using the variables, a logical network computer model to identify one or more attributes of the radiotherapy machine to perform the treatment, the logical network computer model configured to determine the one or more attributes of the radiotherapy machine based on the variable, anatomy data associated with the patient, and the clinic-specific logic; and displaying, by the server on a graphical user interface, the one or more attributes of the radiotherapy machine to perform the treatment.

In another embodiment, a system comprises a radiotherapy machine; and a server in communication with the radiotherapy machine, the server configured to: receive radiation therapy treatment planning data associated with treatment of a patient, the radiation therapy treatment planning data further comprising at least a patient identifier; retrieve, using the patient identifier, anatomy data associated with the patient; retrieve, using a clinic identifier, a file comprising clinic-specific logic indicating treatment attributes of the radiotherapy machine in accordance with at least one of radiation therapy treatment planning data or patient anatomy; execute one or more machine-learning models using the radiation therapy treatment planning data, anatomy data, and clinic-specific logic to identify one or more variables, wherein the one or more machine-learning models is trained based on previously performed radiation therapy treatments and corresponding patient data and clinic-specific logic; execute, using the variables, a logical network computer model to identify one or more attributes of the radiotherapy machine to perform the treatment, the logical network computer model configured to determine the one or more attributes of the radiotherapy machine based on the variable, anatomy data associated with the patient, and the clinic-specific logic; and display, on a graphical user interface, the identified one or more attributes of a radiotherapy machine to perform the treatment.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Figure 1:
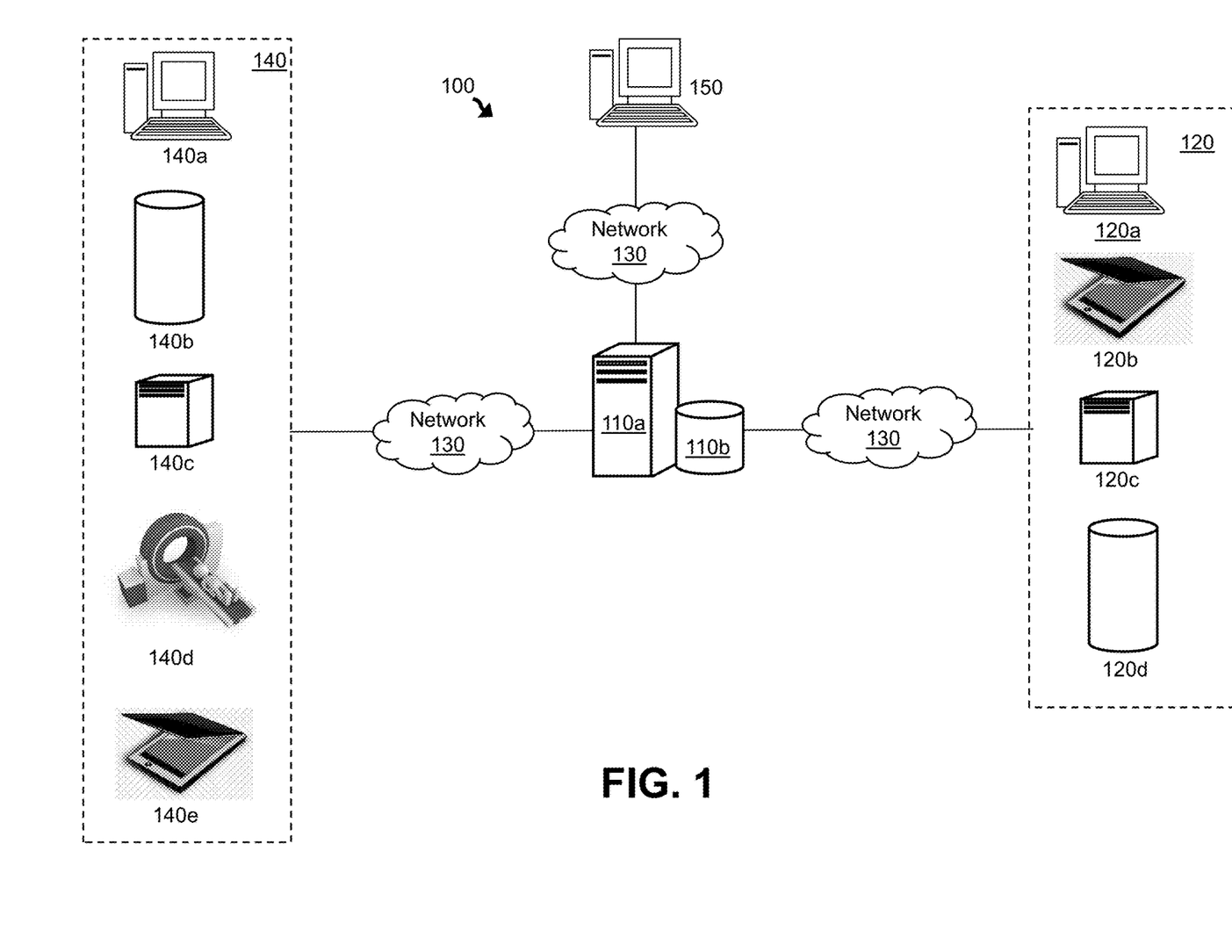
FIG. 1 illustrates components of an RTTP identification system, according to an embodiment.

As will be described below, a central server (referred to herein as the analytics server) can retrieve and analyze data using various methods described herein to identify field geometry for a patient's treatment. FIG. 1 is a non-limiting example of components of a system in which the analytics server operates. The analytics server may utilize features described in FIG. 1 to retrieve data and generate/display field geometry.

FIG. 1 illustrates components of a field geometry identification system 100. The system 100 may include an analytics server 110a, system database 110b, electronic data sources 120a-d (collectively electronic data sources 120), end-user devices 140a-e (collectively end-user device 140), and an administrator computing device 150. The above-mentioned components may be connected to each other through a network 130. The examples of the network 130 may include, but are not limited to, private or public LAN, WLAN, MAN, WAN, and the Internet. The network 130 may include both wired and wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models (including artificial intelligence models) to identify and display RTTP. The electronic platform may include graphical user interfaces (GUI) displayed on each electronic data source 120, the administrator computing device 150, and/or end-user devices 140. An example of the electronic platform generated and hosted by the analytics server 110a may be a web-based application or a website configured to be displayed on different electronic devices, such as mobile devices, tablets, personal computer, and the like. In a non-limiting example, a physician operating the physician device 120b may access the platform, input patient attributes and other data, and further instruct the analytics server 110a to generate an optimized RTTP. The analytics server 110a may then utilize the methods and systems described herein to generate an RTTP and display the results on the end-user devices (e.g., radiotherapy machine 140d). In some configurations, the analytic server 110a may display the RTTP on the physician device 120b itself as well.

The analytics server 110a may host a website accessible to users operating any of the electronic devices descried herein (e.g., end-users), where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110a, in some configurations, the analytics server 110a may include any number of computing devices operating in a distributed computing environment.

The analytics server 110a may execute software applications configured to display the electronic platform (e.g., host a website), which may generate and serve various webpages to each electronic data source 120 and/or end-user devices 140. Different users may use the website to view and/or interact with the predicted results.

The analytics server 110a may be configured to require user authentication based upon a set of user authorization credentials (e.g., username, password, biometrics, cryptographic certificate, and the like). In such implementations, the analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more electronic data sources 120 and/or end-user devices 140. The analytics server 110a may use the data to weigh interaction while training various AI models accordingly. For instance, the analytics server 110a may indicate that a user is a medical professional whose inputs may be monitored and used to train the machine-learning or other computer models described herein.

In some configurations, the analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that is customized according to the user's role defined by the user record in the system database 110b.

The analytics server 110a receives RTTP data (e.g., patient and treatment data) from a user (or retrieve from a data repository), analyzes the data, and displays the results on the electronic platform. For instance, in a non-limiting example, the analytics server 110a may query and retrieve medical images from the database 120d and combine the medical images with RTTP data received from a physician operating the physician device 120b. The analytics server 110a then uses various models (stored within the system database 110b) to analyze the retrieved data. The analytics serve 110a then displays the results (e.g., RTTP including couch and gantry angles) via the electronic platform on the administrator computing device, the end-user devices 140, and/or the electronic physician device 120b.

End-user devices 140 may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic database 140b, clinic server 140c, a medical device, such as a CT scan machine, radiotherapy machine, and the like (140d), clinic device 140e.

The electronic data sources 120 may represent various electronic data sources that contain, retrieve, and/or input data associated with RTTP (e.g., patient data and treatment data). For instance, the analytics server 110a may use the clinic computer 120a, physician device 120b, server 120c (associated with a physician and/or clinic), and database 120d (associated with the physician and/or the clinic) to retrieve/receive RTTP data associated with a particular patient's treatment plan.

The administrator-computing device 150 may represent a computing device operated by a system administrator. The administrator computing device 150 may be configured to display data retrieved, RTTP generated by the analytics server 110a (e.g., various analytic metrics and field geometry) where the system administrator can monitor various models utilized by the analytics server 110a, review feedback, and modify various thresholds/rules described herein.

In operation, a physician may access an application executing on the physician device 120b and input RTTP data (e.g., patient information, patient diagnosis, radiation therapy treatment attributes). The analytics server 110a then uses a patient identifier to query patient data (e.g., patient anatomy and/or medical images) from the electronic data sources 120. The analytics server may then identify a clinic associated with the patient (e.g., clinic performing the treatment) and retrieve one or more files associated with treatment templates and clinic rules. The analytics server 110a may then utilize the systems and methods described herein to generate an optimized/uniform RTTP and display the results onto the physician device 120b, clinic computer 140a, and the medical device 140d (e.g., a display screen of the radiotherapy machine).

The analytics server 110a may be in communications (real time or near real time) with the medical device 140d, such that a server/computer hosting the medical device 140d can adjust the medical device 140d based on the RTTP generated by the analytics server 110a. For instance, the radiotherapy machine may adjust the gantry and couch based on angles and other attributes determined by the analytics server 110a.

Figure 2:
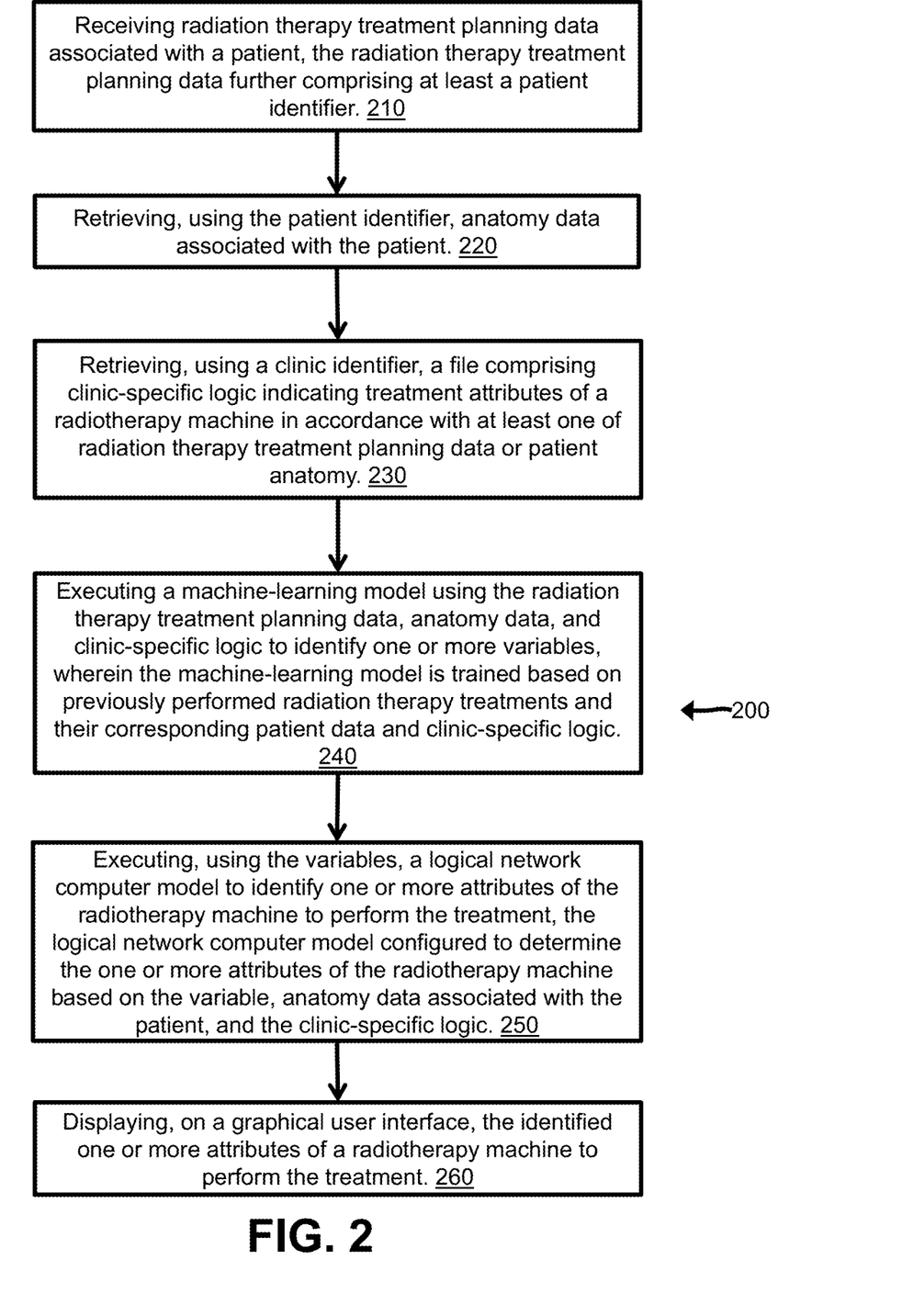
FIG. 2 illustrates a flow diagram of a process executed in an RTTP identification system, according to an embodiment.

FIG. 2 illustrates a flow diagram of a process executed in an RTTP identification system, according to an embodiment. The method 200 includes steps 210-260. However, other embodiments may include additional or alternative execution steps, or may omit one or more steps altogether. The method 200 is described as being executed by a server, similar to the analytics server described in FIG. 1. However, one or more steps of method 200 may also be executed by any number of computing devices operating in the distributed computing system described in FIG. 1. For instance, one or more user computing devices may locally perform part or all the steps described in FIG. 2.

At step 210, the analytics server may receive radiation therapy treatment planning data associated with a patient, the radiation therapy treatment planning data further comprising at least a patient identifier. The analytics server may receive RTTP file associated with one or more patients. The RTTP file may include radiation-therapy-specific information associated with a patient. The RTTP file may refer to a file having data associated with a process in which a medical team (e.g., radiation oncologists, radiation therapist, medical physicists, and/or medical dosimetrists) plan the appropriate external beam radiotherapy or internal brachytherapy treatment techniques for a patient. The RTTP file may include data specific to one or more patient's radiation therapy treatment. In some configurations, the analytics server may receive RTTP data associated with a patient as a result of different medical professionals directly inputting RTTP data into a platform generated/hosted by the analytics server.

The RTTP may include a patient identifier, patient's electronic health data records, medical images (e.g., CT scans, 4D CT Scans, MRIs, and X-ray images), treatment-specific data (e.g., arc information or treatment type), target organ (e.g., specification and location data to identify the tumor to be eradicated). Additional examples may include non-target organs, dosage-related calculations (e.g., radiation dose distribution within an anatomical region of the patient), and radiotherapy machine specific recommendations (e.g., couch-gantry orientations and/or arc information).

At step 220, retrieve, using the patient identifier, anatomy data associated with the patient. The analytics server may use the patient identifier within the RTTP file to identify a particular patient and retrieve additional information regarding said patient. For instance, the analytics server may query one or more databases to identify medical data associated with the patient. For instance, the analytics server may query data associated with the patient's anatomy, such as physical data (e.g., height, weight, and/or body mass index) and/or other health-related data (e.g., blood pressure or other data relevant to the patient receiving radiation therapy treatment). The analytics server may also retrieve data associated with current and/or previous medical treatments received by the patient (e.g., data associated with the patient's previous surgeries).

The analytics server may analyze the data received and generate additional queries accordingly. For instance, the analytics server may retrieve data associated with one or more medical (or other) devices needed for the patient. The analytics server may retrieve data indicating that the patient suffers from a respiratory medical condition. As a result, the analytics server may generate and transmit a query to one or more electronic data sources to identify whether the patient uses/needs a ventilator.

As will be described below, the analytics server may use patient information to identify appropriate field geometry for the patient (e.g., whether a full arc can be recommended for the patient). For instance, if the patient has a body mass index (BMI) that is higher than a predetermined threshold, and/or if the patient is utilizing a ventilator, the analytics server may not recommend a full gantry arc. This may be due to a possibility of the gantry colliding with the patient and/or the patient's ventilator.

If necessary, the analytics server may also analyze the patient's medical data records to identify the needed patient attributes. For instance, the analytics server may query a database to identify the patient's BMI. However, because many medical records are not digitalized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points) the analytics server may execute various image recognition protocols and identify the tumor data.

The analytics server may also receive additional data from one or medical professionals. For instance, a treating oncologist may access a platform generated/hosted by the analytics server and may add, remove, or revise data associated with a particular patient, such as patient attributes, treatment attributes, tumor attributes, primary site of treatment, tumor stage, end-point, whether the primary tumor has been extended, and the like. Because tumor staging and the end level attributes are sensitive information that affect patient treatment, these information is typically inputted by the treating oncologist. In some embodiments, the machine-learning model may identify this information and the treating oncologist may deny, approve, or revise the predicted results. In another example, the treating oncologist may specifically indicate whether the treatment should be unilateral or bilateral.

The data received by the analytics server (e.g., patient/treatment data) may belong to three categories: numerical, categorical, and visual. Non-limiting examples of numerical values may include patient age, physical attributes, and other attributes that describe the patient. Non-limiting examples of categorical values may include different stages of treatment or disease associated with the patient. Visual data may include medical images representing the patient and his/her treatment regions, such as CT scans or other scans illustrating the patient's tumor.

Another example of a patient attribute may include specific tumor locations. More specifically, this data may indicate the primary tumor location with respect to the patient's centerline. This data may be inputted by the treating oncologist or may be analyzed using various image recognition or segmentation methods executed on the patient's medical images. In some embodiments, this information can also be predicted using the machine-learning model if it is not inputted by the treating oncologist (or otherwise received by the analytics server). Another patient attribute may indicate whether and how close the tumor is to other non-diseased organs. For instance, a tumor to be eradicated may be millimeters away from another organ. This information may change field geometry, as other organs must be avoided.

Another example of a patient attribute may include whether the patient uses prosthesis (e.g., hip or femoral head prosthesis). This attribute may result in a change of the patient's treatment (e.g., patients with these conditions might require a special treatment).

At step 230, the analytics server may retrieve, using a clinic identifier, a file comprising clinic-specific logic indicating treatment attributes of a radiotherapy machine in accordance with at least one of radiation therapy treatment planning data or patient anatomy. Each clinic implementing treatment may have its own rules and protocols regarding radiation therapy treatment. The rules may be expressed as a list of logical equations/sentences (e.g., computer readable logic/code) referring to how the clinic usually treats patients. The rules may include conditional sentences or other pre-defined rules depending on one or more attributes of the patients (e.g., patient anatomy and properties).

The analytics server may query one or more electronic data sources to identify clinic-specific treatment files. The analytics server may extract a clinic identifier from the RTTP file or receive an input from a system administrator regarding a treating clinic associated with the patient. In some embodiments, the analytics server may use an identifier of the device inputting the information to determine a clinic associated with the patient. For instance, the analytics server may determine a unique identifier of an electronic device that has accessed a platform hosted or otherwise generated by the analytics server. Using that unique identifier, the analytics server may query a lookup table and identify a corresponding clinic. Additionally or alternatively, the analytics server may receive the clinic-specific rules from a user directly inputting the rules into the platform.

The clinic-specific treatment file may include clinic-specific logic that indicates treatment attributes based on patient attributes or other data received. Therefore, clinic-specific logic may indicate clinic-specific preferences and protocols followed by clinicians and technicians at that particular clinic. Clinic-specific preferences and protocols may not deviate from the treatment plan. However, due to various conditions of a particular clinic or a patient, a clinic may have particular methods of implementing treatment based on patient attributes.

For instance, a patient's RTTP file may indicate that a medical professional (e.g., oncologist) has prescribed radiation of a certain tumor within a certain anatomical region of the patient using a predetermined dose. However, the RTTP file may not indicate specifics of how the treatment must be implemented. In this way, the RTTP file may provide deference to the clinicians and the technicians where the technician will use his/her subject skills to identify the best method of implementing the treatment. Therefore, the clinic-specific rules and protocols do not deviate from or replace the treatment plan, but only supplement them.

In a non-limiting example that illustrates clinic operations, a technician may follow a protocol (e.g., clinic-specific rules) that has been agreed in a clinic to be followed when certain treatment is given. For example, based on a patient's BMI, the technician may determine to place the isocenter in the middle of the tumor and have a full arc gantry motion while the beam is on. As used herein, the isocenter (or the radiation isocenter) refers to the point in space where radiation beams intersect when the gantry rotates (e.g., half or full arcs) during the "beam-on" mode. However, for a second patient with a different BMI, the technician may determine to implement the same treatment by having a few fixed tube directions that are evenly distributed and attempt to avoid certain structure/organs of the patient's body. Therefore, while both patients receive similar treatments (that are similarly recorded in their respective RTTP files), each patient receives different implementations and procedures.

In another non-limiting example illustrating clinic rules, a particular clinic-specific rule may indicate that a patient having physical attributes (e.g., height and weight) that satisfy a threshold will receive volumetric modulated arc therapy (VMAT) treatment in two arcs. As used herein, VMAT refers to a radiation therapy technique that delivers the radiation dose continuously as the treatment machine rotates. The clinic-specific rules may indicate that, unless expressly stated by the treating doctor, the default radiotherapy methods should be VMAT radiation having two arcs. Another clinic may use other methods or may require fewer or more number of arcs. In another non-limiting example, a clinic-specific rule may dictate that if a patient is connected to a ventilator, the radiation therapy treatment should include two partial arcs.

The analytics server may retrieve the file comprising clinic-specific logic where the logic has been codified accordingly. For instance, the analytics server or a system administrator may have previously generated the file that includes all clinic-specific logic in logical sentences that are readable/executable by a computer/analytics server. The analytics server may use Markov Logic Networks (MLNs) to represent the clinic-specific rules framework. The analytics server may generate the field geometry selection process as a decision tree of rules using the MLN process. Codifying the clinic-specific rules as MLN allows the analytics server to represent each logic as either a hard rule (categorically required to be true or false or having a weight that is higher than a threshold, such as 1.0) or soft rule (supplementing the hard rules or having weights, such as 0.3 or 0.5). As MLN is based on a statistical approach, it can codify partially conflicting soft rules.

Figure 3:
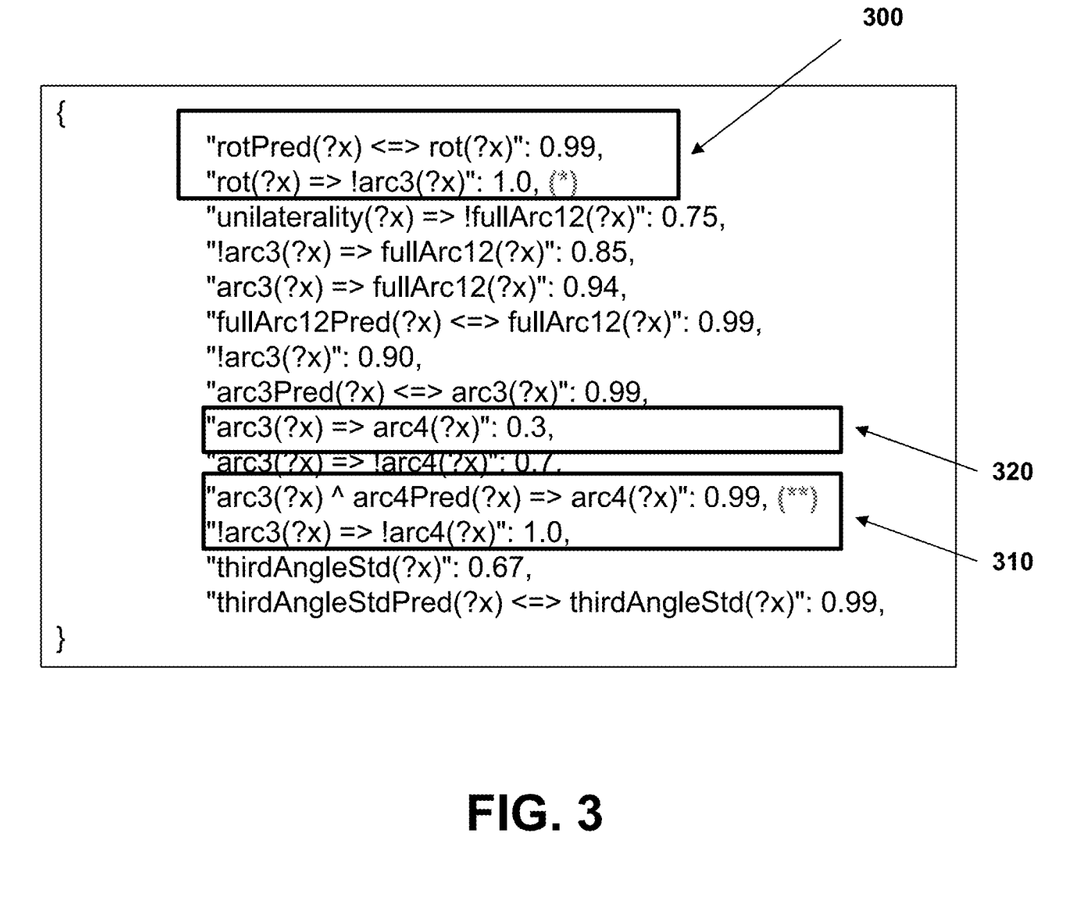
FIGS. 3-5 illustrate examples of computer models described herein, according to an embodiment.

The analytics server may generate a file for each clinic where each file represents the clinic-specific rules and procedures previously codified in a computer-readable language format. When prompted, the analytics server may then use a clinic identifier to retrieve a file associated with a particular clinic. Referring now to FIG. 3, a non-limiting example of clinic-specific rules codified in computer language is illustrated. For instance, rule 300 indicates that "if the couch is rotated (if rot=True), then do not use a third non-rotated VMAT arc (arc3=False)". The code 300 also indicates that the weight (importance) of the code 300 is 1.0 (e.g., indicating that this is a hard rule that must be satisfied when in conflict with other rules). The code 310 indicates, "if at least three VMAT arcs are used and any evidence/data associated with a fourth arc also exists (e.g., the machine-learning model or a when a user predicts four arcs), then a fourth VMAT arc is used."

In another example, code 320 represents a statistical probability rule that may have been calculated using the clinic's prior radiation therapy treatments. As depicted, the weight (importance) of code 320 is 0.3 (below 0.5), which deemphasizes the rule for selecting the fourth VMAT arc. However, if another rule, such as 310, influences the selection of the fourth VMAT arc with a great importance, then the selection of the fourth VMAT arc could be favored, since the resultant overall probability for the fourth VMAT arc may be greater than 0.5.

The code depicted in FIG. 3 represents statistical probability rules that may be included in a particular clinic's rules and procedures. The analytics server may generate these rules via mining the clinic's database for prior cases and identifying relevant statistical probabilities, especially when no other definite rules for choosing certain details of the radiation therapy treatment exist. For instance, when a definite rule exists (e.g., if attribute A is present, then two arcs are selected), the analytics server may assign a 1.0 weight to the rule. However, if multiple rules are not definite, the analytics server may analyze previous treatments and identify a corresponding important/weight associated with each rule, as described above.

In some configurations, the analytics server may utilize a machine-learning approach to identify corresponding weight factors for the clinic-specific rules. A machine-learning model may be trained using previously performed treatments of a clinic, such that the machine-learning model can identify a corresponding weight (repressing an importance factor) associated with each attribute. For instance, treatment data may be ingested by the machine-learning model in a supervised and/or unsupervised manner in conjunction with patient data for each particular treatment. Additionally, codified clinic-specific rules may also be ingested by the machine-learning model. The machine-learning model may then use various clustering and training methods to identify an appropriate weight, variable, and/or parameter for each clinic-specific rule (e.g., 0.3 for rule 320).

Referring back to FIG. 2, at step 240, the analytics server may execute a machine-learning model using the radiation therapy treatment planning data, anatomy data, and clinic-specific logic to identify one or more variables, wherein the machine-learning model is trained based on previously performed radiation therapy treatments and their corresponding patient data and clinic-specific logic. The machine-learning model may utilize various artificial intelligence modeling techniques to identify one or more attributes associated with the patient. For instance, the machine-learning model may utilize a neural network or spiking neural network, logical regression, or other artificial intelligence modeling methods to create a model that represents previously performed radiation therapy treatments, their corresponding patient attributes, and RTTP files in view of each clinic's clinic-specific logic. For instance, the analytics server may generate a training dataset (ground truth) consisting of radiation therapy treatments performed by one or more clinics. For each previously performed treatment, the analytics server may also gather patient data and corresponding RTTP file. The analytics server may also supplement this data by different files representing clinic specific rules, as described above.

In a non-limiting example, the analytics server trains the machine-learning model based on a previously performed radiation therapy treatment of a patient. The machine-learning model may ingest patient data (as described above) at the time of treatment and the patient's RTTP file. Therefore, the machine-learning model identifies how a particular clinic used its clinic-specific rules to implement treatment of a patient. The machine-learning model may uncover hidden patterns connecting patient and/or treatment attributes to the way radiation therapy treatment was performed (e.g., field geometry).

The analytics server may train the machine-learning model, such that when the analytics server inputs a new patient's data (e.g., data retrieved in steps 210-230), the machine-learning model predicts various attributes, weights, and variables that indicate field geometry for the new patient at his/her treating clinic.

When the analytics server executes the machine-learning model, the analytics server calculates an optimized solution for the set of patient attributes. Therefore, the analytics server calculates, in a statistical sense, the probability estimates for each attribute of field geometry. In particular, using the machine-learning model may generate parameters and variables that can be included when executing/querying the logical network computer model. As described herein, the analytics server may utilize the logic network computer model to ensure that no hard rules (for example any strict clinic's protocol) are violated. Additionally, the analytic server may use the machine-learning model to identify variables, weight, and parameter that optimize soft rules identified within the clinic-specific rules.

The analytics server may execute the trained machine-learning model using the data gathered in steps 210-230. As a result, the analytics server receives, from the machine-learning model, one or more variables and/or weights. As will be described below, the analytics server may execute another model using the predicted variable and weights to identify an optimized field geometry for the patient.

At step 250, the analytics server may execute, using the variables, a logical network computer model to identify one or more attributes of the radiotherapy machine to perform the treatment, the logical network computer model configured to determine the one or more attributes of the radiotherapy machine based on the variable, anatomy data associated with the patient, and the clinic-specific logic.

Similar to the files corresponding to logic of each clinic described in step 230, the logical network computer model may be a set of predefined rules expressed in logical sentences for a particular clinic. In some configurations, the logical network computer model for a clinic may include same logical rules as the clinic-specific rules described above. The logical network computer model may be a computer model configured to receive variables generated by the machine-learning algorithm, patient data and other data retrieved by the analytics server and identify radiotherapy attributes (e.g., field geometry) associated with a patient's treatment. Therefore, the logical network computer model may include the clinic-specific rules in addition to other rules that can calculate field geometry.

For example, the logical network computer model may comprises of two categories of logical rules. The first type are absolute type of rules that are not weighted and are not dependent upon subjective understanding of the technician (e.g., hard rules). For instance, one rule may indicate that when a medical professional (e.g., the treating oncologist) has indicated a treatment type (e.g., VMAT or IMRT), then the treatment must follow the medical professional's decision. Therefore, this rule does not include any weights or variable to be interpreted using technicians' subjective understanding.

The second type of logical rules may include rules having fuzzy weights and/or variables. For instance, different patient attributes and treatment attributes may be weighted differently to achieve a uniform result (field geometry). For instance, a tumor's attribute (e.g., how close the tumor is to another organ or the tumor's position relative to the patient's centerline) may be weighted higher than other patient attributes (e.g., height or BMI). In another example, tumor stage information (e.g., cancer stage) may be weighted higher than tumor's proximity to other organs. For instance, a tumor that has developed dangerously and is in an advanced stage may be treated differently than another tumor that is positioned at the same location but is in early stages (e.g., more advanced tumor might be more aggressively eradicated).

The analytics server may execute the logical network computer model using the patient attributes and data predicted via the machine-learning model. For instance, the analytics server may execute the logical network computer model by inputting the patient attributes collected from various electronic data sources (steps 210 and 220). The analytics server may execute code corresponding to hard rules (e.g., rules with high weights that satisfy a threshold, such as 1.0) to identify various field geometry attributes. The analytics server may also input results predicted by the machine-learning model. For instance, the analytics server may input one or more weights/variables predicted by the machine-learning model. The analytics server may apply these variables/weights to optimize the field geometry for each patient (soft rules).

Therefore, the analytics server may combine patient data directly received from one or more electronic data sources (e.g., patient attributes, data received from the treating oncologist) and variables received from the machine-learning models to identify field geometry based on hard and soft rules. In some configurations, the analytics server may not overwrite the hard rules even if the machine-learning model identifies a conflicting result (e.g., variables that would lead to conflicting result). For instance, if the analytics server calculates two arcs using the hard rules, the analytics server may dismiss variables, received from the machine-learning model that identify three arcs. As a result, the analytics server may comply with hard rules identified by each clinic while optimizing other field geometry parameters using soft rules.

The analytics server may execute the logical network computer model using the variables received from executing the machine-learning model to identify appropriate field geometry. In a non-limiting example, a particular rule within the logical network computer model may be a formula including variables for oral cavity, tumor size (e.g., endpoints), and a unilateral treatment suggested by the oncologist. Based on these three variables, the formula may determine a nodal region to which the patient will receive ipsilateral radiation treatment.

The analytics server may execute/query the logical network computer model based on specific regions. For instance, the analytics server may execute the model and query whether different nodes within a patient's body are to be treated. For instance, the analytics server queries whether region A (e.g., predefined region) is going to be treated. If the answer is no, the analytics server may then move to a next region (e.g., region B identifying another predefined region of the patient). If the answer to the first query is a yes, then the analytics server further queries specific information regarding the treatment of region A, such as couch angle, gantry arcs, and the like.

Figure 4:
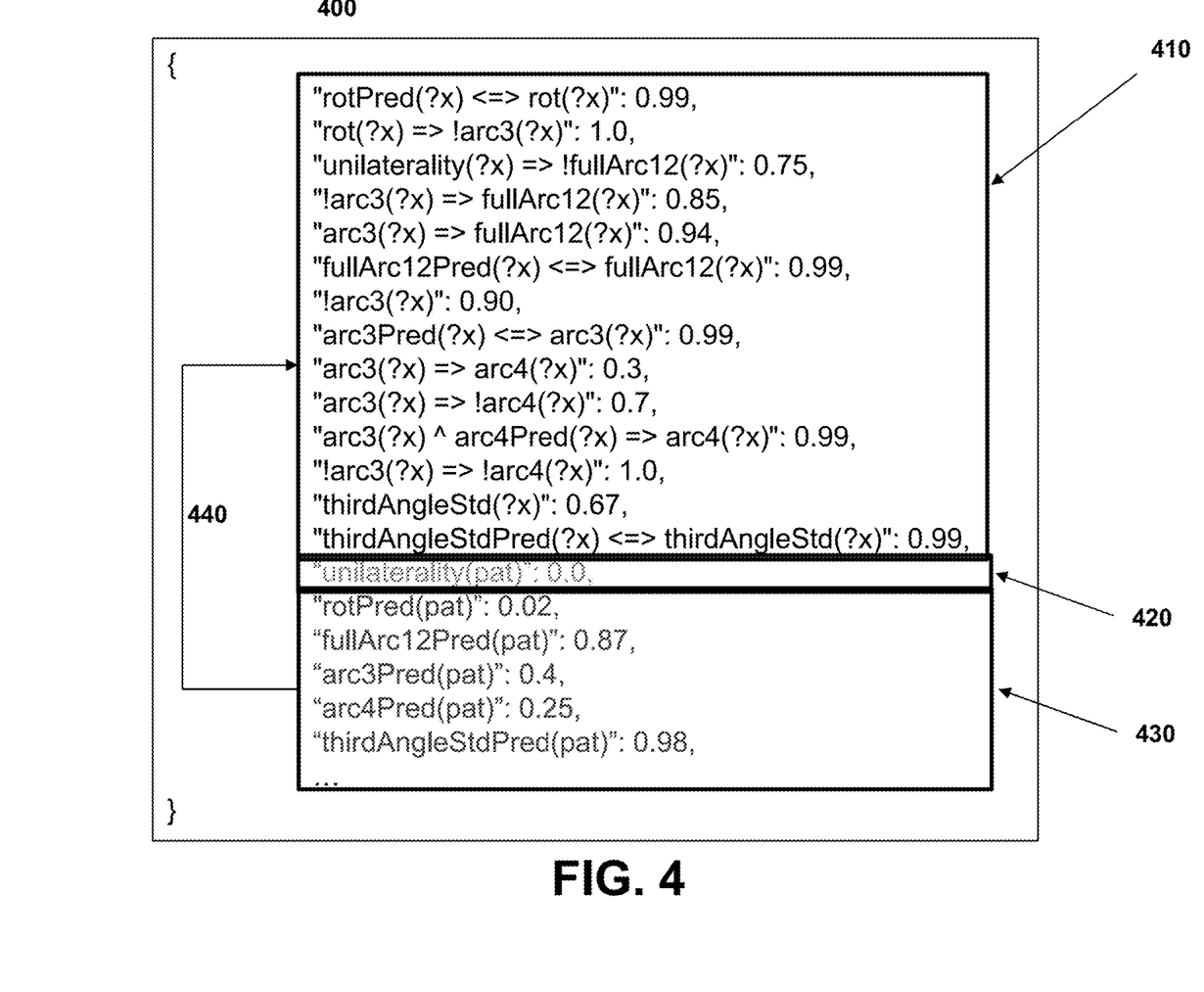

Referring now to FIG. 4, a non-limiting example of computer readable code representing the logical network computer model is illustrated. The logical network computer model 400 includes code 410 that is similar to the code depicted in FIG. 3. The code 410 illustrates clinic-specific rules for a particular clinic that has been previously codified. The code 420 illustrates that a user (e.g., treating oncologist) has previously inputted that the treatment of the patient is not a unilateral treatment. Finally, code 430 illustrates values calculated using the machine-learning model. Using the values depicted in code 430, the analytics server may execute the code 410 to identify an optimized field geometry (440).

As depicted, code 430 represents machine-learning predictions (binary values or probabilities) for a particular patient. Specifically, "rotPred" predicts if the couch is rotated, "fullArc12Pred" predicts if the two first arcs are full arcs, "arc3Pred" predicts if a third arc is used, "arc4Pred" predicts if a fourth arc is used, and "thirdAngleStdPred" predicts if the third collimator angle is a standard angle used by the clinic. The machine-learning models can use data to predict a value for each of the above-referenced attributes. The predicted values can be directly calculated by the machine-learning model or deduced from the accuracy of the machine-learning model. The analytics server may then use the predicted values and execute the code 410 to identify field geometry.

Before displaying the results or otherwise outputting the results generated upon executing/querying the logical network computer model, the analytics server may verify the predicted results using one or more dynamic template computer models. The dynamic template computer model may be another computer model comprising a set of rules expressed in computer readable and mathematical coding. These templates may then identify various acceptable standards, such as thresholds, tolerances, and the like. The analytics server may determine whether the generated field geometry complies with the predetermined rules of the dynamic templates.

The dynamic template computer model may be a codified set of rules that are used to verify the accuracy of the results generated using the methods and systems described herein. For instance, the analytics server may determine whether a couch angle (generated using the systems and methods described herein) is more or less than a predetermined threshold. If the analytics server determines that the couch angle is appropriately calculated (the angle is within acceptable range), the analytics server may move to the next step 260. However, if the analytics server determines that the angle is outside the range, the analytics server may generate and transmit a notification to one or more electronic devices described herein. For instance, the analytics server may alert the physician device, system administrator, clinic computer, and/or the technician device that the predicted results are not within appropriate ranges. Additionally or alternatively, the analytics server may iteratively perform the above-described calculations to achieve better results (e.g., select the second option achieved instead of the first option that was unacceptable).

The dynamic template computer model may also be specific to a clinic. For instance, the dynamic template computer model may represent clinic-specific rules and thresholds that must be complied with when calculating field geometry. Furthermore, executing the dynamic template may be an obligatory part of the process. For instance, a system administrator may instruct the analytics server to execute the dynamic template each time before rendering the results generated upon querying/executing the logical network computer.

Referring back to FIG. 2, at step 260, displaying, on a graphical user interface, the identified one or more attributes of a radiotherapy machine to perform the treatment. The analytics server may display the results on a graphical user interface (such as on a monitor associated or on the radiotherapy machine). For instance, the analytics server may display the field geometry onto a graphical user interface associated with the radiotherapy machine where one or more technicians can use the identified field geometry to align the patient's body and implement the radiation therapy treatment. In another example, the analytics server may display the identified field geometry onto a graphical user interface of a clinic (e.g., on a monitoring rooms computer or any other computer associated with the clinic). In another example, the analytics server may display the identified field geometry onto a graphical user interface displayed on any other medical professional's computer, such as the treating oncologist's computer where the information can be reviewed and/or verified.

Figure 5:
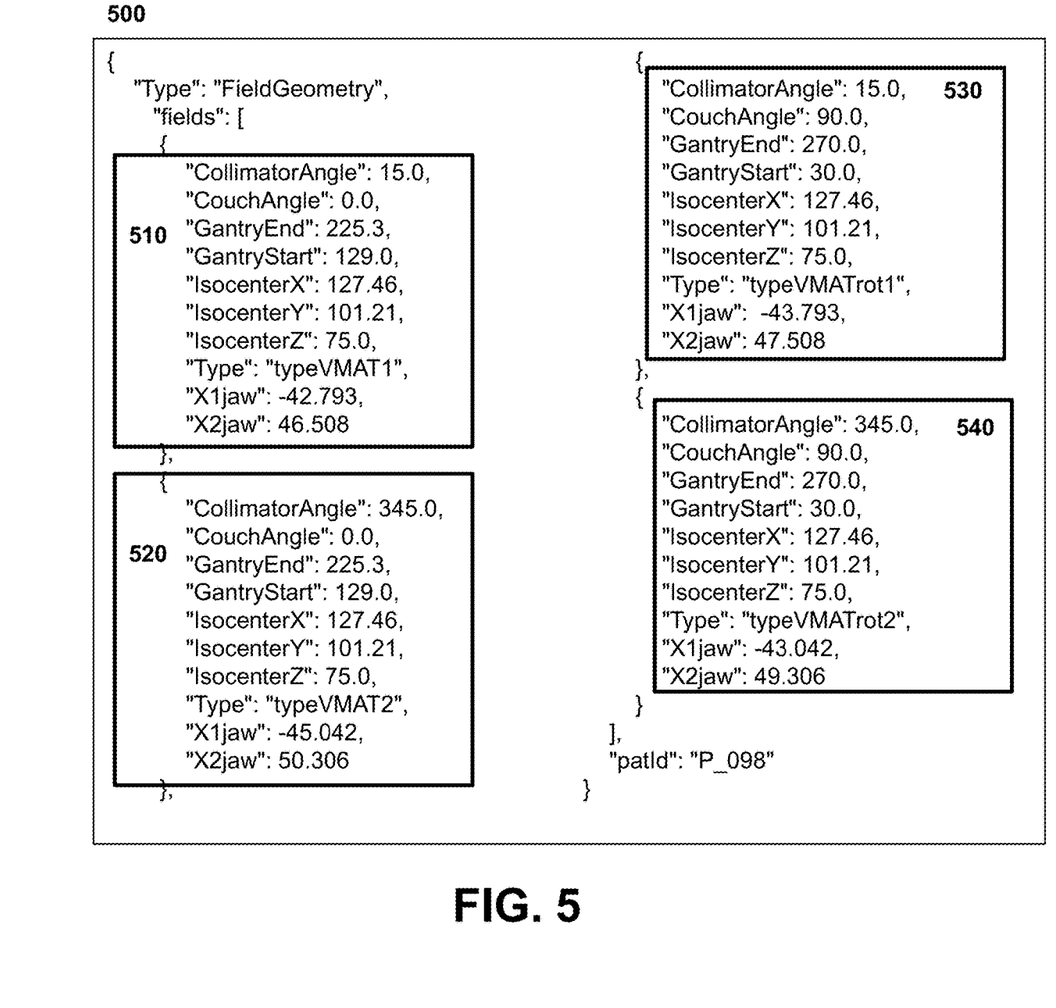

The graphical user interface 500 may display the finalized field geometry values for each VMAT arc. For instance, for a particular patient's treatment, the analytics server identifies four VMAT arcs where each arc includes different field geometry as depicted in graphical components 510-550. For each arc, the analytics server may calculate and display a collimator angle, couch angle gantry endpoint, gantry start thing point, isocenter location attributes (in each axis), VMAT type, X1 and X2 jaw values. The end-user (e.g., technician and/or treating oncologist or any other medical professional viewing the graphical user interface 500) may add, revise, and/or overwrite any of the depicted values.

The analytics server may monitor each user's interaction with the graphical user interface 500. The analytics server may use the user's interactions to train and revise the computer models described herein, such as the machine-learning model. Therefore, the graphical user interface 500 may represent a "first field geometry suggestion," which may or may not be accepted by the end-user. If any of the values is not considered desirable or appropriate, the rejected values can also be used as an additional data to the method 200. As a result, the analytics server may generate a secondary suggested field geometry. Using this iterative method, the analytics server may improve the field geometry and the computer models described herein.

Using the methods and systems described herein, the analytics server can have a formalized approach to generate a field geometry in a single automated framework based on various variables, parameters, and settings that depend on patient, the patient's treatment, and/or the clinic. The methods and systems described herein enable a central server to generate field geometry that is optimized and does not depend on the technician's subjective skills and understanding.

Additionally or alternatively, the analytics server may communicate with the radiotherapy machine and/or a host server operatively in communication with the radiotherapy machine to modify and revise the radiotherapy machine's configurations. For instance, the analytics server may determine field geometry for a patient. The analytics server may then identify a radiotherapy machine implementing the patient's treatment. The analytics server also determines the patient's field geometry using methods and systems described herein. The analytics server then instructs the radiotherapy machine (e.g. by transmitting executable instruction files to the host server) to adjust its configurations according to the identified field geometry. For instance, the analytics server may instruct the radiotherapy machine to adjust its couch angles according to the calculated/optimized field geometry.

The analytics server may also monitor various end-users interactions with the identified data to improve the results by revising and retraining the machine-learning model. The analytics server may monitor the electronic device viewing the field geometry to identify interactions between the end user and the electronic device while the electronic device is outputting the results. Based on the end-users interactions (e.g., approval, denial, and/or modification of the results), the analytics server may then revise and retrain the machine-learning model.

When the user performs an activity on the electronic platform, the analytics server may track and record details of the user's activity. For instance, when a predicted result is displayed on the user electronic device, the analytics server may monitor to identify whether the user has interacted with the predicted results by editing, deleting, accepting, or revising the results. The analytics server may also identify a timestamp of each interaction, such that the analytics server records the frequency of modification, duration of revision/correction.

The analytics server may utilize an application-programming interface (API) to monitor the user's activities. The analytics server may use an executable file to monitor the user's electronic device. The analytics server may also monitor the electronic platform displayed on an electronic device via a browser extension executing on the electronic device. The analytics server may monitor multiple electronic devices and various applications executing on the electronic devices. The analytics server may communicate with various electronic devices and monitor the communications between the electronic devices and the various servers executing applications on the electronic devices.

In some embodiments, the analytics server may monitor the data packages received and sent by each electronic device to monitor the content of what is displayed/executed/modified on the electronic device. The communication may take any suitable form. For example, the electronic device may execute an application (e.g., browser extension) having an executable file that enables a user to navigate to the electronic platform (e.g., web site).

The analytics server may use several techniques to track user's activities on the electronic device, such as by tracking browser cookies and/or screen-scraping protocols. In another example, the analytics server may track the user activity by periodically retrieving user's web browser cookies. The analytics server may transmit cookies to a system database where they can be analyzed (e.g., in batches) to identify user activities.

In some configurations, the analytics server may monitor the electronic device using an executable file (application) installed as a browser extension. The browser extension (executable file) may be executing as a background process of the electronic device. For instance, the browser extension may be transparent to the user operating the electronic device. In this way, the analytics server is able to monitor the user's activities without disturbing the user and/or obfuscating the display screen of the electronic device. In some embodiments, the analytics server may activate a monitoring module (e.g., browser extension or executable file) upon outputting the results on the electronic platform.

The analytics server may use the data collected/monitored to train the machine-learning model and improve its predicted results. In order to train the machine-learning model, the analytics server may generate new training datasets.

The analytics server may monitor whether an end user accepted the predicted results. The analytics server may generate a metric corresponding to a frequency that a certain predicted result was accepted, denied, or revised. If the predicted results were accepted, the analytics server assumes that the predicted results were satisfactory to the end user. If the user revised the predicted results, the analytics server assumes that they were partially satisfactory to the user. Finally, if the user denied the predicted results, the analytics server assumes that they were completely unsatisfactory. The analytics server may also generate a metric for how frequently predicted results generated by a model is accepted, revised, and/or denied.

As described above, when a user revises a predicted result, the analytics server monitors the revision performed by the user. In some embodiments, the analytics server displays a predicted result on the electronic platform. However, the users feel the need to perform minor corrections before they are satisfied with the results. The analytics server may monitor this correction and generate training datasets accordingly. For instance, the analytics server may monitor a time duration that each user spent correcting the predicted results. The analytics server may assume that a higher this monitored time duration corresponds to more inaccurate the results.

In some embodiments, the analytics server may also monitor the corrections themselves and use this data to train the machine-learning model. For instance, training and revising the machine-learning model may be proportionally implemented based on the end-users modifications. For instance, the analytics server may generate a training data set that includes the amounts of corrections inputted by the user (e.g., whether the user revised the results by 10% or 80%).

The analytics server may always display a prompt requesting users' feedback. In some embodiments, the analytics server may display the prompt based on a predetermined frequency (e.g., 50% of instances where a predicted result is displayed). Furthermore, the analytics server may select the users receiving the prompt based on predetermined rules. For instance, the analytics server may select the users randomly. In some configurations, the predetermined rules may require the analytics server to display the prompt for users who satisfy a certain threshold (e.g., only for users who have three or more years of experience or only treating oncologist and not technicians).

The analytics server may train the machine-learning model using the above-described training datasets. The analytics server may use various methods to train the machine-learning model, such as supervised and/or unsupervised learning methods. For instance, the analytics server may use one or more of the following machine-learning approaches to train the machine-learning model: regression, classification, clustering, dimensionality reduction, ensemble methods, neural nets and deep learning, transfer learning, reinforcement learning, and the like. In some embodiments, the analytics server may periodically train the machine-learning model. For instance, the analytics server may collect/monitor user interactions and store the corresponding data. The analytics server may then use a predetermined frequency (e.g., once a month or once a week) to train the machine-learning model using the stored training datasets. A system administrator can modify the frequency of the batch training.

Additionally or alternatively, the analytics server may train the machine-learning model when the model produces results that receive feedback that satisfies a threshold. For instance, the analytics server trains the model when the results outputted on the electronic platform receive a feedback (e.g., thumbs down or modification/revision of the results by the users) more frequently than a predefined threshold (e.g., 40% of time).

Additionally or alternatively, the analytics server may train the model based on a customized (predetermined) segmentation of training data and/or users. For instance, the analytics server may segment the training data before training the AI model. The analytics server may train the AI model in a customized and segmented manner that is meaningfully tethered to the end users' needs. In a non-limiting example, the analytics server may train the AI model based on feedback received from a selection of users (e.g., users who work at a particular clinic or users who satisfy a certain score). As a result, the analytics server may customize the machine-learning model for a particular clinic. This training method allows the machine-learning model to adapt to the particular clinic and produce results that are more acceptable to the users within that clinic.

Non-Limiting Example

Figure 6:
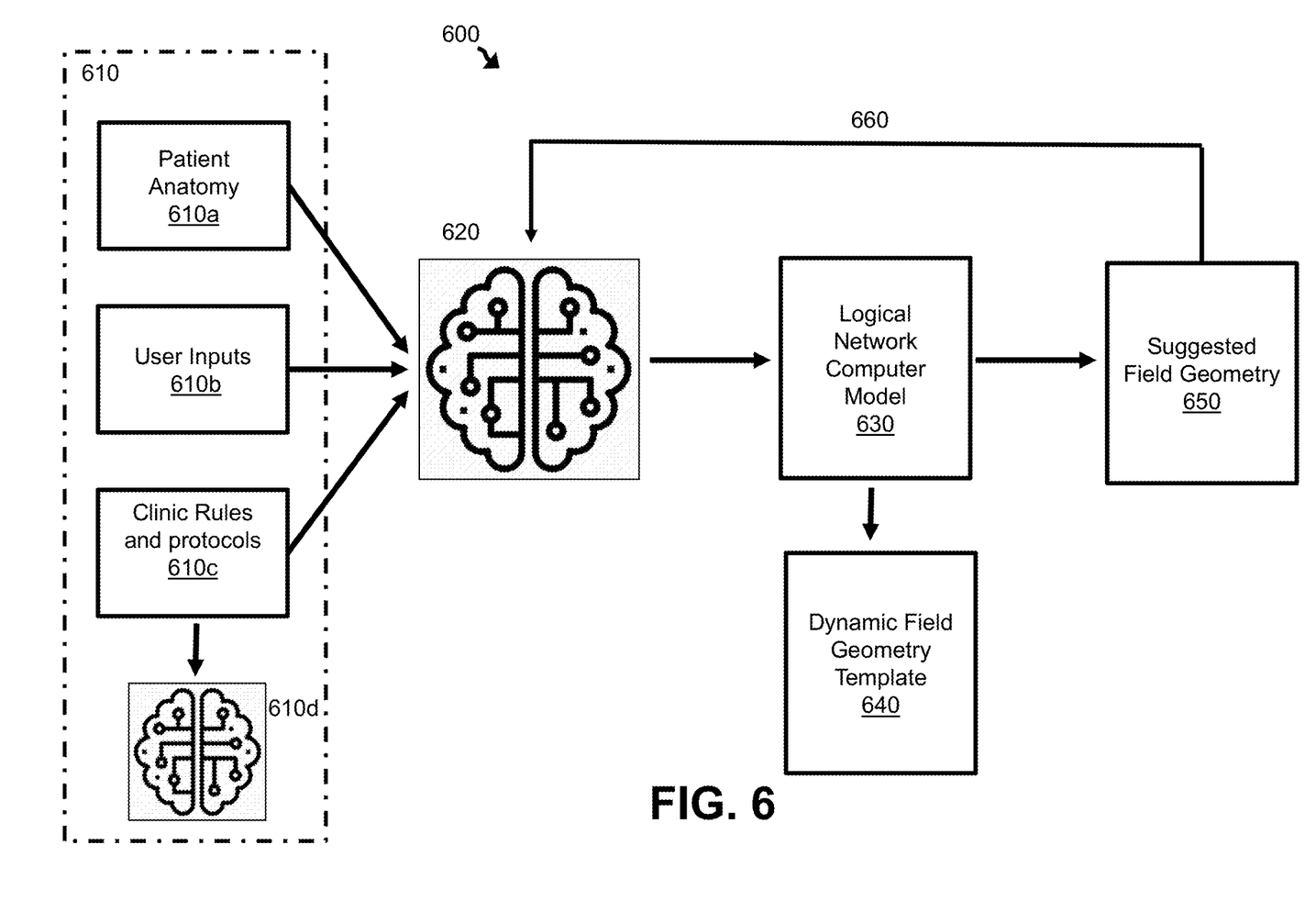
FIG. 6 illustrates a flow diagram of a process executed in an RTTP identification system, according to an embodiment.

Referring now to FIG. 6, a non-limiting visual example of a workflow utilizing the methods and systems described herein is illustrated. In this non-limiting example 600, the analytics server identifies field geometry for a patient's treatment. The analytics server may first collect patient data 610. The patient data may include patient anatomy data 610a, user inputs 610b (received from treating oncologist), and clinic-specific rules 610c for the clinic conducting the patient's treatment. As discussed above, the analytics server may first codify the clinic-specific rules in logical sentences. The analytics server may then train a machine learning model 610d using previously performed radiation therapy treatments, corresponding patient data, and the codified clinic-specific rules. The trained machine-learning model 610d may then identify various weights/parameters associated with each clinic-specific rule. The clinic-specific rule 610c may also include hard rule that do not have any weights/variables or have variables/weights that are higher than a certain threshold.

The analytics server may receive the patient's RTTP file and extract the needed patient data 610. The analytics server then executes the machine-learning model 620 using the patient data 610, such that the machine-learning model 620 ingests the patient data and calculates weights and variables that are then inputted in the logical network computer model 630.

As described above, the machine-learning model 620 is trained using previously performed treatments and their corresponding patient data, RTTP files, user inputs, and clinic-specific rules for the corresponding clinic. The machine-learning model may be trained using data associated with different (e.g., all) clinics. Additionally or alternatively, the analytics server may limit its training to a particular clinic or a group of similar clinics. As a result of executing the machine-learning model 620, the analytics server calculates variables and weight associated with the particular clinic conducting the patient's treatment (because the analytics server execute the machine-learning model 620 using clinic rules and protocols for the particular clinic conducting the patient's treatment).

Using the calculated variables, the analytics server executes (e.g., queries) a logical network computer model 630 that is specific to the clinic conducting the patient's treatment. As a result, the analytics server calculates field geometry for the patient's treatments. The analytics server evaluates the predicted field geometry against predetermined tolerances and threshold indicated in the dynamic field geometry template 640 and displays the suggested field geometry 650. The analytics server also monitors technician (or other medical professionals) interactions with the suggested results and re-trains the machine-learning model 620 accordingly (e.g., based on the actual choices of the technician as monitored by the analytics server, 660). Even though FIG. 6 displays two separate machine-learning models (610d and 620), in some configurations, these machine learning models can be combined in to one machine-learning model.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   receiving, by a server, radiation therapy treatment planning data associated with treatment of a patient, the radiation therapy treatment planning data further comprising at least a patient identifier;
   retrieving, by the server using the patient identifier, anatomy data associated with the patient; retrieving, by the server using a clinic identifier for a clinic implementing the treatment of the patient, a file comprising clinic-specific logic indicating clinic-specific rules with corresponding weights for identifying treatment attributes of a radiotherapy machine in accordance with at least one of radiation therapy treatment planning data or the anatomy data;
   executing, by the server, one or more machine-learning models using the radiation therapy treatment planning data, anatomy data, and clinic-specific logic to identify one or more variables, wherein the one or more machine-learning models are trained based on previously performed radiation therapy treatments and previous patient data associated with the previously performed radiation therapy treatments and clinic-specific logic;
   executing, by the server using the variables, a logical network computer model to identify one or more attributes of the radiotherapy machine to perform the treatment by ingesting the one or more variables generated via the machine-learning model, the logical network computer model configured to use the clinic-specific logic to determine the one or more attributes of the radiotherapy machine based on the one or more variables, anatomy data associated with the patient, and the clinic-specific logic with corresponding weights; and
   displaying, by the server on a graphical user interface, the one or more attributes of the radiotherapy machine to perform the treatment.

2. The method of claim 1, further comprising:
   transmitting, by the server, an instruction to a radiotherapy machine to modify itself based on the identified one or more attributes.

3. The method of claim 1, wherein the graphical user interface is displayed on the radiotherapy machine.

4. The method of claim 1, wherein the graphical user interface is displayed on at least one of a physician device or an electronic device associated with a clinic conducting the treatment.

5. The method of claim 4, wherein the server monitors whether a user interacts with at least one attribute displayed on the graphical user interface.

6. The method of claim 5, wherein the server trains the one or more machine-learning models based on the interaction.

7. The method of claim 1, wherein the identified attribute is angle associated with a couch or a gantry of the radiotherapy machine.

8. The method of claim 1, wherein the identified attribute is a rotation or arc attribute of a gantry associated with the radiotherapy machine.

9. The method of claim 8, wherein the rotation or arc attribute corresponds to whether a gantry of the radiotherapy machine conducting the treatment has a full or partial arc.

10. The method of claim 1, further comprising:
    comparing, by the server, the identified one or more attributes of a radiotherapy machine against one or more predetermined thresholds.

11. A system comprising:
    a radiotherapy machine; and
    a server in communication with the radiotherapy machine, the server configured to:
      receive radiation therapy treatment planning data associated with treatment of a patient, the radiation therapy treatment planning data further comprising at least a patient identifier;
      retrieve, using the patient identifier, anatomy data associated with the patient;
      retrieve, using a clinic identifier for a clinic implementing the treatment of the patient, a file comprising clinic-specific logic indicating clinic-specific rules with corresponding weights for identifying treatment attributes of the radiotherapy machine in accordance with at least one of radiation therapy treatment planning data or anatomy data;
      execute one or more machine-learning model using the radiation therapy treatment planning data, anatomy data, and clinic-specific logic to identify one or more variables, wherein one or more machine-learning models are trained based on previously performed radiation therapy treatments and previous patient data associated with the previously performed radiation therapy treatments and clinic-specific;
      execute, using the variables, a logical network computer model to identify one or more attributes of the radiotherapy machine to perform the treatment by ingesting the one or more variables generated via the machine-learning model, the logical network computer model configured to use the clinic-specific logic to determine the one or more attributes of the radiotherapy machine based on the one or more variables, anatomy data associated with the patient, and the clinic-specific logic with corresponding weights; and
      display, on a graphical user interface, the identified one or more attributes of a radiotherapy machine to perform the treatment.

12. The system of claim 11, wherein the server is further configured to:
    transmit an instruction to a radiotherapy machine to modify itself based on the identified one or more attributes.

13. The system of claim 11, wherein the graphical user interface is displayed on the radiotherapy machine.

14. The system of claim 11, wherein the graphical user interface is displayed on at least one of a physician device or an electronic device associated with the clinic.

15. The system of claim 14, wherein the server monitors whether a user interacts with at least one attribute displayed on the graphical user interface.

16. The system of claim 15, wherein the server trains the one or more machine-learning models based on the interaction.

17. The system of claim 11, wherein the identified attribute is angle associated with a couch or a gantry of the radiotherapy machine.

18. The system of claim 11, wherein the identified attribute is a rotation or arc attribute of a gantry associated with the radiotherapy machine.

19. The system of claim 18, wherein the rotation or arc attribute corresponds to whether a gantry of the radiotherapy machine conducting the treatment has a full or partial arc.

20. The system of claim 11, wherein the server is further configured to:
compare the identified one or more attributes of a radiotherapy machine against one or more predetermined thresholds.

* * * * *